United States Patent
Heitzmann et al.

(10) Patent No.: US 7,595,723 B2
(45) Date of Patent: Sep. 29, 2009

(54) WIRELESS COMMUNICATION PROTOCOL FOR A MEDICAL SENSOR SYSTEM

(75) Inventors: Harold A. Heitzmann, Irvine, CA (US); John A. Frazier, Costa Mesa, CA (US); Morgan T. McKeown, Irvine, CA (US); Wayne A. Noda, Mission Viejo, CA (US); George Francis Sutton, III, La Jolla, CA (US); Ann B. Yadlowsky, Irvine, CA (US); Michael LeRoy Gelvin, Alta Loma, CA (US); John T. Armstrong, Pasadena, CA (US); John D. Richert, La Habra Heights, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 361 days.

(21) Appl. No.: 11/449,511

(22) Filed: Jun. 7, 2006

(65) Prior Publication Data

US 2007/0109117 A1     May 17, 2007

Related U.S. Application Data

(60) Provisional application No. 60/756,691, filed on Jan. 6, 2006, provisional application No. 60/736,408, filed on Nov. 14, 2005.

(51) Int. Cl.
*G08B 1/08* (2006.01)
(52) U.S. Cl. .............. 340/539.12; 340/10.2; 340/573.1; 340/870.11; 340/870.16; 600/300
(58) Field of Classification Search ............... 340/10.1, 340/10.2, 10.5, 10.51, 870.07, 870.11, 870.16, 340/573.1, 572.1, 539.11, 539.12; 600/300
See application file for complete search history.

(56) References Cited

U.S. PATENT DOCUMENTS

| 4,360,030 | A | 11/1982 | Citron et al. |
|---|---|---|---|
| 4,751,726 | A | 6/1988 | Hepp et al. |
| 4,958,645 | A | 9/1990 | Cadell et al. |
| 4,970,900 | A | 11/1990 | Shepherd et al. |
| RE33,518 | E | 1/1991 | McCord et al. |
| 4,981,141 | A | 1/1991 | Segalowitz |

(Continued)

FOREIGN PATENT DOCUMENTS

DE    10029205 A1    1/2002

(Continued)

OTHER PUBLICATIONS

Digital Wireless Corporation, "WIT915 Frequency Hopping Transceiver OEM Module," .pdf file from website www.digital-wireless.com, undated.

*Primary Examiner*—Thomas J Mullen
(74) *Attorney, Agent, or Firm*—Gregory J. Carlin

(57) ABSTRACT

In one embodiment the present invention provides a wireless communication system for medical sensor data. This communications system includes a portable unit that connects to a wireless sensor and a monitor unit that connects to a sensor monitor. Once activated, the units will self organize into a wireless communication structure controlled by the portable unit. As other pairs of units activate, they can self-organize their transmissions by joining an existing network or by creating new networks.

39 Claims, 8 Drawing Sheets

U.S. PATENT DOCUMENTS

| | | | |
|---|---|---|---|
| 5,012,411 A | 4/1991 | Policastro et al. |
| 5,036,869 A | 8/1991 | Inahara |
| 5,205,294 A | 4/1993 | Flach et al. |
| 5,307,818 A | 5/1994 | Segalowitz |
| 5,381,798 A | 1/1995 | Burrows |
| 5,387,194 A | 2/1995 | Williams et al. |
| 5,394,879 A | 3/1995 | Gorman |
| 5,400,794 A | 3/1995 | Gorman |
| 5,417,222 A | 5/1995 | Dempsey et al. |
| 5,458,122 A | 10/1995 | Hethuin |
| 5,488,631 A | 1/1996 | Gold et al. |
| 5,490,515 A | 2/1996 | Mortara |
| 5,538,007 A | 7/1996 | Gorman |
| 5,566,676 A | 10/1996 | Rosenfeldt et al. |
| 5,579,001 A | 11/1996 | Dempsey et al. |
| 5,617,871 A | 4/1997 | Burrows |
| 5,634,468 A | 6/1997 | Platt et al. |
| 5,640,960 A | 6/1997 | Jones et al. |
| 5,664,270 A | 9/1997 | Bell et al. |
| 5,723,853 A | 3/1998 | Longacre, Jr. et al. |
| 5,748,103 A | 5/1998 | Flach et al. |
| 5,751,797 A | 5/1998 | Saadeh |
| 5,752,918 A | 5/1998 | Fowler et al. |
| 5,767,791 A | 6/1998 | Stoop et al. |
| 5,848,971 A | 12/1998 | Fowler et al. |
| 5,855,550 A | 1/1999 | Lai et al. |
| 5,862,803 A | 1/1999 | Besson et al. |
| 5,865,733 A | 2/1999 | Malinouskas et al. |
| 5,871,451 A | 2/1999 | Unger et al. |
| 5,882,300 A | 3/1999 | Malinouskas et al. |
| 5,913,827 A | 6/1999 | Gorman |
| 5,926,144 A | 7/1999 | Bolanos et al. |
| 5,944,659 A | 8/1999 | Flach et al. |
| 5,957,854 A | 9/1999 | Besson et al. |
| 5,959,529 A | 9/1999 | Kail, IV |
| 6,080,690 A | 6/2000 | Lebby et al. |
| 6,093,146 A | 7/2000 | Filangeri |
| 6,097,848 A | 8/2000 | Salvati |
| 6,139,503 A | 10/2000 | Müller |
| 6,150,951 A | 11/2000 | Olejniczak |
| 6,164,284 A | 12/2000 | Schulman et al. |
| 6,208,889 B1 | 3/2001 | Gorman |
| 6,213,942 B1 | 4/2001 | Flach et al. |
| 6,238,338 B1 | 5/2001 | DeLuca et al. |
| 6,267,723 B1 | 7/2001 | Matsumura et al. |
| 6,285,899 B1 | 9/2001 | Ghaem et al. |
| 6,287,252 B1 | 9/2001 | Lugo |
| 6,289,238 B1 | 9/2001 | Besson et al. |
| 6,304,774 B1 | 10/2001 | Gorman |
| 6,364,834 B1 | 4/2002 | Reuss et al. |
| 6,370,117 B1 | 4/2002 | Koraitim et al. |
| 6,407,993 B1 | 6/2002 | Moulsley |
| 6,440,068 B1 | 8/2002 | Brown et al. |
| 6,441,747 B1 | 8/2002 | Khair et al. |
| 6,458,086 B1 | 10/2002 | Franco et al. |
| 6,468,219 B1 | 10/2002 | Njemanze |
| 6,475,153 B1 | 11/2002 | Khair et al. |
| 6,493,568 B1 | 12/2002 | Bell et al. |
| 6,496,705 B1 | 12/2002 | Ng et al. |
| 6,497,659 B1 | 12/2002 | Rafert |
| 6,504,834 B1 | 1/2003 | Fifield |
| 6,529,738 B1 | 3/2003 | Forde et al. |
| 6,533,729 B1 | 3/2003 | Khair et al. |
| 6,544,173 B2 | 4/2003 | West et al. |
| 6,544,174 B2 | 4/2003 | West et al. |
| 6,553,336 B1 | 4/2003 | Johnson et al. |
| 6,558,320 B1 | 5/2003 | Causey, III et al. |
| 6,563,913 B1 | 5/2003 | Kaghazian |
| 6,577,893 B1 | 6/2003 | Besson et al. |
| 6,589,170 B1 | 7/2003 | Flach et al. |
| 6,608,557 B1 | 8/2003 | Menard et al. |
| 6,611,705 B2 | 8/2003 | Hopman et al. |
| 6,616,606 B1 | 9/2003 | Petersen et al. |
| 6,629,284 B1 | 9/2003 | Leermakers |
| 6,669,630 B1 | 12/2003 | Joliat et al. |
| 6,673,015 B1 | 1/2004 | Glover et al. |
| 6,678,312 B1 | 1/2004 | Mohindra |
| 6,694,180 B1 | 2/2004 | Boesen |
| 6,716,165 B1 | 4/2004 | Flanders et al. |
| 6,731,976 B2 | 5/2004 | Penn et al. |
| 6,740,033 B1 | 5/2004 | Olejniczak et al. |
| 6,749,566 B2 | 6/2004 | Russ |
| 6,764,446 B2 | 7/2004 | Wolinsky et al. |
| 6,773,396 B2 | 8/2004 | Flach et al. |
| 6,805,667 B2 | 10/2004 | Christopherson et al. |
| 6,814,702 B2 | 11/2004 | Redano |
| 6,850,788 B2 | 2/2005 | Al-Ali |
| 6,855,115 B2 | 2/2005 | Fonseca et al. |
| 6,856,832 B1 | 2/2005 | Matsumura et al. |
| 6,858,006 B2 | 2/2005 | MacCarter et al. |
| 6,897,788 B2 | 5/2005 | Khair et al. |
| 6,987,965 B2 | 1/2006 | Ng et al. |
| 2001/0023315 A1 | 9/2001 | Flach et al. |
| 2001/0034475 A1 | 10/2001 | Flach et al. |
| 2002/0013517 A1 | 1/2002 | West et al. |
| 2002/0013518 A1 | 1/2002 | West et al. |
| 2002/0044059 A1 | 4/2002 | Reeder et al. |
| 2002/0109621 A1 | 8/2002 | Khair et al. |
| 2002/0115914 A1 | 8/2002 | Russ |
| 2002/0161308 A1 | 10/2002 | Matsumura et al. |
| 2002/0165436 A1* | 11/2002 | Schluter et al. ............ 600/300 |
| 2003/0033032 A1* | 2/2003 | Lind et al. .................... 700/52 |
| 2003/0105403 A1 | 6/2003 | Istvan et al. |
| 2003/0199777 A1 | 10/2003 | Hopman et al. |
| 2003/0206116 A1 | 11/2003 | Weiner et al. |
| 2003/0214408 A1 | 11/2003 | Grajales et al. |
| 2004/0002305 A1 | 1/2004 | Byman-Kivivuori et al. |
| 2004/0015058 A1 | 1/2004 | Besson et al. |
| 2004/0054352 A1 | 3/2004 | Adams et al. |
| 2004/0072475 A1 | 4/2004 | Istvan |
| 2004/0073127 A1 | 4/2004 | Istvan et al. |
| 2004/0102683 A1 | 5/2004 | Khanuja et al. |
| 2004/0127802 A1 | 7/2004 | Istvan et al. |
| 2004/0186358 A1 | 9/2004 | Chernow et al. |
| 2004/0199056 A1 | 10/2004 | Husemann et al. |
| 2004/0225199 A1 | 11/2004 | Evanyk et al. |
| 2004/0225203 A1 | 11/2004 | Jemison et al. |
| 2004/0268132 A1 | 12/2004 | Waris |
| 2005/0038345 A1 | 2/2005 | Gorgenberg et al. |
| 2005/0038346 A1 | 2/2005 | Miele |
| 2005/0043641 A1 | 2/2005 | Ueda |
| 2005/0102167 A1 | 5/2005 | Kapoor |
| 2005/0151640 A1* | 7/2005 | Hastings ............... 340/539.11 |
| 2006/0247505 A1* | 11/2006 | Siddiqui .................... 600/300 |

FOREIGN PATENT DOCUMENTS

| | | | |
|---|---|---|---|
| DE | 10123226 A1 | 11/2002 |
| DE | 10301225 A1 | 2/2004 |
| EP | 0458883 B1 | 8/1990 |
| EP | 0707825 A2 | 4/1996 |
| EP | 0770349 A1 | 5/1997 |
| EP | 1038496 A1 | 9/2000 |
| EP | 1060704 A2 | 12/2000 |
| EP | 1070479 A2 | 1/2001 |
| EP | 1099407 A2 | 5/2001 |
| EP | 1262144 A1 | 12/2002 |
| GB | 2150332 A | 6/1985 |
| GB | 2243691 A | 11/1991 |
| JP | 56-003833 | 7/1982 |
| JP | 57-118471 | 7/1982 |
| JP | 57-006129 | 7/1983 |
| WO | WO 87/06113 A1 | 10/1987 |
| WO | WO 90/09143 A1 | 8/1990 |

| | | |
|---|---|---|
| WO | WO 95/07048 A1 | 3/1995 |
| WO | WO-97/18639 | 5/1997 |
| WO | WO 97/18639 A1 | 5/1997 |
| WO | WO 98/00056 A1 | 1/1998 |
| WO | WO 98/20793 A1 | 5/1998 |
| WO | WO 99/13766 A1 | 3/1999 |
| WO | WO 01/78831 A2 | 10/2001 |
| WO | WO 02/064032 A2 | 8/2002 |
| WO | WO 02/078775 A2 | 10/2002 |
| WO | WO 03/061465 A2 | 7/2003 |
| WO | WO 03/088830 A1 | 10/2003 |
| WO | WO 2004/002301 A2 | 1/2004 |
| WO | WO 2004/072888 A2 | 8/2004 |

* cited by examiner

Figure 5

| Message Section Name | Bits | Description |
|---|---|---|
| Preamble | 32 | |
| Synch | 32 | Unique synch word for each frequency channel to facilitate synching the message |
| Unique ID | 23 | Provides a unique identification number designating the message origin |
| Unit Type | 1 | Designates the unit type, such as a portable unit or a monitor unit |
| Fill | 1 | Rounds message out to even number of bytes |
| Timeslot Number | 5 | Number for 26 timeslots plus control timeslot may be possible |
| Timing Master | 1 | If set, other portable units should be adjusting their time base to stay in step with this unit. |
| Synced/Availability | 1 | This communication shows if the portable unit is synching with a timing master<br><br>If portable unit is timing master, it communicates the number of open timeslots |
| Sensor Connected | 1 | Indicates whether a sensor is connected |
| Command | 3 | Communicates commands to the monitor unit such as:<br><br>DATA – indicates sensor data is present in the message<br><br>POWER_DOWN – indicates portable unit will power down<br><br>NEW_LINK – establishes initial contact with M mate and gives it a new ID<br><br>JUMP – tells the monitor unit to jump to a different frequency channel<br><br>RSSI – contains the RSSI values for other units<br><br>OPEN_SLOTS – sends the number of slots available on frequency channel (transmitted by timing master whenever another command is not being sent) |
| Data | 60 | Contains the sensor data. This data can be "whitened" by inverting every other sample to reduce any biases that may change the sensor readings. |
| Command Data | 8 | Provides data needed for some commands sent to the monitor unit. For example, the jump frequency channel number, RSSI values, and open timeslot numbers (for timing master only) |
| CRC | 16 | Error correction data within the message allowing the receiving unit to determine if any errors are present within the message. |
| Guard | 8 | Non coding bits |
| Total Bits | 192 | |

Figure 6

| Message Section Name | Bits | Description |
|---|---|---|
| Preamble | 32 | |
| Synch | 32 | Unique synch word for each frequency channel to facilitate synching the message |
| Unique ID | 23 | Provides a unique identification number designating the message origin |
| Unit Type | 1 | Designates the unit type, such as a portable unit or a monitor unit |
| Timeslot Number | 5 | Number for 26 timeslots plus control timeslot may be possible |
| Synced | 1 | This communication shows if the portable unit is synching with a timing master |
| Fill | 6 | Rounds message out to even number of bytes |
| Reply | 4 | Provides reply commands to the portable unit such as: NEW_LINK_INTIMATE confirms initial contact with portable unit and lets portable unit know that it is paired with another portable unit NEW_LINK_UNRESTRICTED to confirm initial contact with X mate and let X know that it is not intimate with another unit JUMP_REPLY indicates the new channel the monitor unit is jumping to DATA_GOOD indicates that the data message was successfully received POWERING_DOWN indicates that the monitor unit is powering down |
| Reply Data | 8 | Provides data needed for some reply commands sent back to the portable unit, such as RSSI values |
| CRC | 16 | Error correction data within the message allowing the receiving unit to determine if any errors are present within the message. |
| Guard | 10 | Non coding bits |
| Total Bits | 138 | |

Figure 7

| Message Section Name | Bits | Description |
|---|---|---|
| Preamble | 32 | |
| Synch | 32 | Unique synch word for each frequency channel to facilitate synching the message |
| Unique ID | 23 | Provides a unique identification number designating the message origin |
| Unit Type | 1 | Designates the unit type, such as a portable unit or a monitor unit |
| Timeslot Number | 6 | Number for 63 timeslots plus control timeslot may be possible |
| Command | 2 | Communicates commands to the timing master such as:<br><br>SLOT_REQUEST to ask the timing master for a timeslot that it can use<br><br>JUMP to tell monitor units (and nearby portable units) to jump to new channel |
| Command Data | 4 | Provides data needed for some commands sent to the monitor unit. For example, the jump frequency channel number |
| CRC | 16 | Error correction data within the message allowing the receiving unit to determine if any errors are present within the message. |
| Guard | 15 | Non coding bits |
| Total Bits | 131 | |

Figure 8

| Message Section Name | Bits | Description |
|---|---|---|
| Preamble | 32 | |
| Synch | 32 | Unique synch word for each frequency channel to facilitate synching the message |
| Unique ID | 23 | Provides a unique identification number designating the message destination |
| Timeslot Number | 6 | Number for 26 timeslots plus control timeslot may be possible |
| Unit Type | 1 | Designates the unit type, such as a portable unit or a monitor unit |
| Reply | 9 | Provides reply commands to the portable unit such as:<br><br>OPEN_SLOT indicating the number and location of open timeslots<br><br>CHANNEL_FULL indicates that a frequency channel is full<br><br>RSSI_REQUEST indicates a request for RSSI data<br><br>JUMP indicates a frequency channel that will be jumped to |
| CRC | 16 | Error correction data within the message allowing the receiving unit to determine if any errors are present within the message. |
| Guard | 15 | Non coding bits |
| Total Bits | 134 | |

WIRELESS COMMUNICATION PROTOCOL FOR A MEDICAL SENSOR SYSTEM

RELATED APPLICATIONS

This application claims priority to U.S. Provisional Application Ser. No. 60/756,691, filed Jan. 6, 2006 entitled Wireless Communication Protocol For A Medical Sensor System; and 60/736,408, filed Nov. 14, 2005 entitled Wireless Communication Protocol For A Medical Sensor System; the contents of which are incorporated by references. This application also incorporates by reference U.S. Non-Provisional application Ser. No. 11/292,872, filed Dec. 2, 2005 entitled Wireless Communication System For Pressure Monitoring.

BACKGROUND OF THE INVENTION

One important aspect to delivering satisfactory care to patients within a hospital setting is monitoring different biological indicators used to diagnose medical conditions. For example, the careful monitoring of blood pressure, heartbeat rate, and EKG can help determine a patient's current health and future chances for recovery. Traditionally, this monitoring has been achieved by attaching sensors to a patient and then connecting these sensors to monitor units which display the sensor readings.

A sensor cable has been the simplest and most reliable means of connecting these sensors with a nearby patient monitor. However, these cables tangle easily, limit the distance of the patient from the monitor and can become damaged over time.

More recently, wireless communication methods have been used between the sensor and the patient monitor, overcoming many of the disadvantages presented by traditional cable systems. Some typical examples of these wireless systems can be seen in U.S. Pat. Nos. 5,748,103; 5,862,803; 6,441,747; 6,544,174; and 6,850,788; the contents of which are herein incorporated by reference.

Generally, wireless medical communications systems have included two popular types of system architectures: simple independent systems that transmit directly to a sensor monitor, such as U.S. Pat. No. 5,862,803, and more complex hospital-wide telemetry systems having sensor networks throughout a hospital, such as U.S. Pat. No. 6,544,174. Simple wireless sensor systems often include sensors that transmit medical data to specialized monitors near the patient. However, these systems are designed for use with only a few sensors and therefore tend to inefficiently use bandwidth. Further, using many of these units within a hospital can lead to interference between transmissions of nearby systems.

The more complex medical telemetry systems often include wireless receivers throughout the hospital connecting to a central server computer, allowing sensors to transmit data at nearly any location within the hospital. Additionally, these wireless transmitter systems are often designed to make more efficient use of the designated bandwidth and so are less likely to cause interference with nearby units. However, the size and complexity of these systems dramatically increases the expense for a hospital. Further, such complexity tends to reduce the reliability of the data transmissions, as well as the overall reliability of the system.

What is needed is a wireless communication system for medical sensors that combines the reliability of the simpler wireless sensor communication systems with the efficiency and reduced interference found in more complex telemetry systems.

OBJECTS AND SUMMARY OF THE INVENTION

It is an object of the present invention to overcome the limitations of the prior art.

It is another object of the present invention to provide a wireless communications system that self-organizes sensor communications over wireless frequencies.

It is another object of the present invention to provide a wireless communications system having a network-organizing master that is portable.

It is another object of the present invention to provide a wireless communications system that increases the stability of wireless networks.

It is another object of the present invention to provide a wireless communications system that does not require a master controller administering the wireless communications.

It is another object of the present invention to provide a wireless communications system that does not require a central server to administer.

The present invention attempts to achieve these objects, in one embodiment, by providing a wireless communication system for medical sensor data. This communications system includes a portable unit that connects to a wireless sensor and a monitor unit that connects to a sensor monitor. Once activated, the units will self organize into a wireless communication structure controlled by the portable unit. As other pairs of units activate, they can self-organize their transmissions by joining an existing network or by creating new networks.

BRIEF DESCRIPTION OF THE DRAWINGS

FIG. 5 illustrates a message structure of a portable unit according to a preferred embodiment of the present invention;

FIG. 6 illustrates a message structure of a stationary unit according to a preferred embodiment of the present invention;

FIG. 7 illustrates a control message structure of a portable unit according to a preferred embodiment of the present invention; and FIG. 8 illustrates a control message structure of a stationary unit according to a preferred embodiment of the present invention.

DETAILED DESCRIPTION OF THE INVENTION

Wireless Communications Protocol Overview

Figure 1:
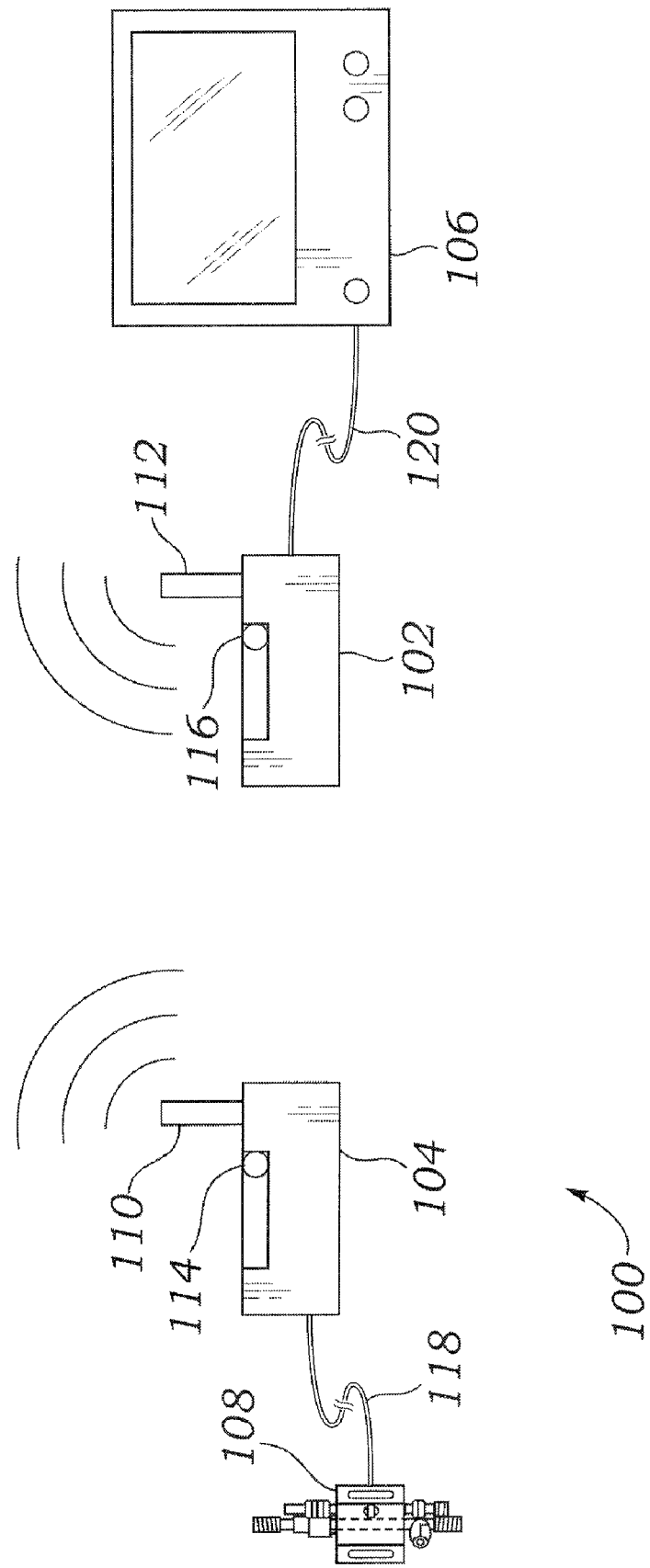
FIG. 1 illustrates a wireless communication system according to a preferred embodiment of the present invention.

Generally speaking, a preferred embodiment of the present invention is directed to a communication protocol or algorithm that facilitates data transfer between a portable sensor transmitter on a patient and a monitor for displaying the sensor data. This communication protocol not only organizes data transmissions between a single pair of a sensor transmitter and a monitor (also referred to generally as a "device pair") but allows "self-organization" of multiple device pairs within a close proximity to each other. By organizing communications between multiple device pairs, interference between multiple device pairs is reduced and the bandwidth of limited wireless frequencies is maximized, increasing data transmission reliability and the number of device pairs that can be used within close proximity.

The communication protocol combines some qualities of a TDMA communication protocol with that of an FDMA protocol to achieve organization around multiple frequency channels that each have a plurality of transmission timeslots. Typically, communications protocols that include some form of timeslots, such as TDMA, require a master communication organizer (generally referred to as a "master") that maintains a master time clock and tells other transmitter units (generally referred to as "slaves") in the networks which timeslot they can send data in. Traditionally, these masters are a single stationary unit since their constant transmissions typically require more power which is easier facilitated by the constant power of an AC outlet.

In the communication protocol of the present preferred embodiment, the portable, battery-operated sensor transmitter acts as a master, organizing timeslots and designating them for use with specific device pairs. However, instead of only one master for a communication network, each frequency can have its own master that controls the timeslots for that frequency. Further, if a frequency lacks a master, a non-master sensor transmitter can "take charge" and become a master, ensuring that if a master is shut off, ceases communications, or otherwise becomes unavailable, another sensor transmitter will take its place.

In this respect, instead of organizing around a single, unchanging, unmoving master, the communication protocol organizes around one master per frequency that may change from one sensor transmitter to another. The communication protocol network is therefore more dynamic than traditional network structures, allowing device pairs to switch frequencies, timeslots, and even their "status" as a master or slave.

To prevent every sensor transmitter from constantly fighting for control of a frequency as the master, a "line of succession" or hierarchy is created, constantly updated, and distributed to all of the sensor transmitters on a specific channel. Thus, all sensor transmitters on a frequency are always aware of which sensors transmitters are next in line to become masters. So, when the current master drops out, whichever sensor transmitter is "number two" in the line of succession becomes the master of that frequency.

To help each master with its organizational duties, such as assigning timeslots to device pairs for sending data, each frequency has a control timeslot, or a timeslot that is known to be reserved solely for organizational control communications between the current master and any other sensor transmitter nearby. In other words, when any commands or requests are transmitted to or from the master, the control timeslot is used for the transmissions, leaving the remaining timeslots available for transmission of sensor data.

In some situations, a slave sensor transmitter may have trouble communicating with its master due to, for example, a weak signal. If the slave sensor transmitter finds another frequency channel with a stronger master signal, it can jump over to that frequency by sending a timeslot request on the control channel of the new frequency. If the frequency has an open timeslot, its information will be transmitted back to the slave on the control timeslot, allowing the slave sensor transmitter and its sensor monitor (i.e. device pair) to join the new frequency and transmit on its new timeslot. If the new frequency does not have a new timeslot, the master instead sends a refusal signal on the control timeslot and the slave continues searching for a new frequency channel to join.

Occasionally, a slave sensor transmitter will not find a frequency channel with a suitable master. In this situation, the slave sensor transmitter can choose an empty frequency and become the master, allowing other slave sensor transmitters to join the frequency as needed.

When a sensor transmitter starts up, has decided to jump to a new frequency, or is otherwise looking for a new frequency channel to join, it will prefer to join a frequency that already includes another close device pair. Such a preference can minimize interference caused by the close proximity of these device pairs. More specifically, when two device pairs are close to each other, their transmissions can bleed into nearby frequencies, causing interference. However, if both nearby device pairs transmit on the same frequency, they transmit on different timeslots and therefore never transmit at the same time, preventing interference.

Before a device pair can join the communications network, and specifically a frequency channel, a sensor transmitter and a sensor monitor must be mated or paired together. By pairing a sensor transmitter and a sensor monitor together, each unit is aware of an ID number that distinguishes the other, thus telling each unit where to send communication data.

These units are not manufactured as device pairs. Instead, users can pair separate transmitters and monitors as desired. This pairing can be achieved by providing a user with an RFID token that can transmit a pairing ID to each unit, which in turn allows each unit to send and listen for the pairing ID and thus identify each other. The RFID token is positioned near a sensor transmitter and a sensor monitor which both read the pairing ID. The sensor transmitter first searches for an appropriate frequency channel, then requests a timeslot from the master of that frequency. Once a timeslot is obtained, the sensor transmits the RFID pairing ID so that it can be identified by the sensor monitor which is searching for the same pairing ID. Once the units "find" each other, they exchange permanent unit ID numbers which allows each unit to identify its paired unit.

In this respect, a user establishes communications between a sensor transmitter and a sensor monitor by pairing the two units by exchanging the same pairing ID, then allowing the sensor transmitter to join an existing frequency network as a slave or start a new frequency network as a master. In either case, a timeslot on a frequency is determined which allows the sensor transmitter to transmit sensor data to the sensor monitor.

Wireless Communications Protocol Embodiment

While the previous description generally described a preferred embodiment of the present invention, another description of the present invention is presented in greater detail below.

FIG. 1 illustrates a preferred embodiment of a wireless communications system 100 that utilizes the wireless communication protocol of the present invention. In this preferred embodiment, a portable unit 104 is connected via a cable 118 to a pressure transducer 108 for obtaining the blood pressure of a patient. While a blood pressure transducer 108 will be discussed in the present preferred embodiment, other medical sensors may also be used, such as heart rate sensors and ECG electrodes.

The portable unit 104 obtains the sensor data from the pressure transducer 108, digitizes the data, and then incorporates the data and other relevant information into a transmission packet. The transmission packet is wirelessly transmitted, preferably by radio frequency, to a monitor unit 102 which extracts the sensor data from the transmission packet and communicates it via cable 120 to the monitor 106. A more thorough description of this operation is set forth in U.S. Non-Provisional application Ser. No. 11/292,872, filed Dec. 2, 2005 entitled Wireless Communication System For Pressure Monitoring which is commonly owned with the present application, and which is incorporated herein by reference.

As will be described in greater detail below, the transmission packets are preferably coordinated by a TDMA/FDMA system having multiple time channels on each frequency channel used. Unlike prior art systems, the portable unit 104, not the monitor unit 102, acts as a timekeeper or master, controlling and coordinating the communications between multiple pairs of units 102 and 104. Additionally, when multiple pairs of units 102 and 104 are activated near each other, they self-organize their communications, as generally described in the overview above, to prevent collisions and maximize the use of designated frequency and time channels.

Frequency Channels and Timeslots

Figure 2:
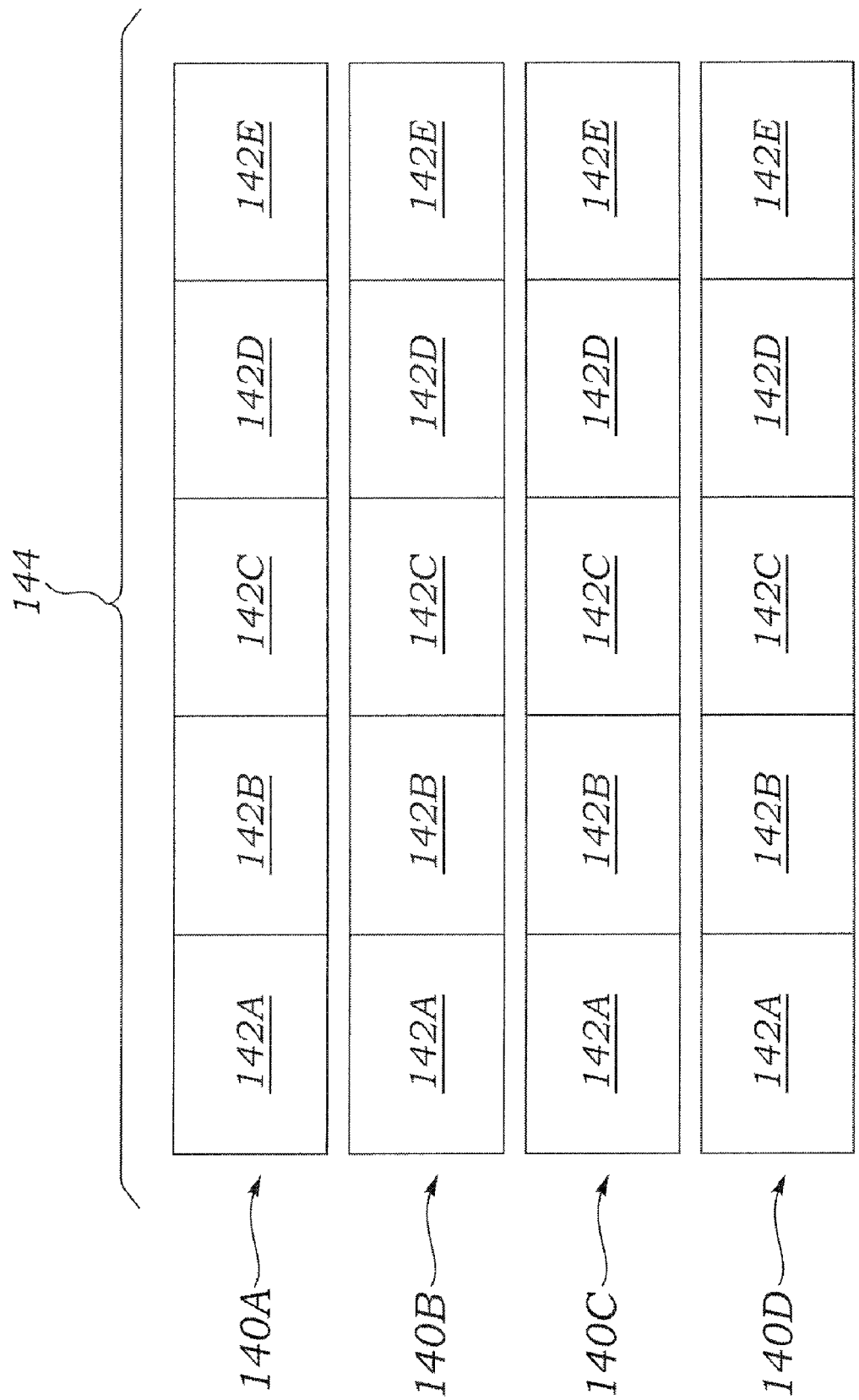
FIG. 2 illustrates a communications protocol structure according to a preferred embodiment of the present invention.

In a preferred embodiment, the wireless protocol used according to the present invention transmits data in a format that combines TDMA characteristics with those of FDMA protocols. More specifically, since the frequency range and therefore the number of frequencies for such wireless transmission is often limited (e.g. by FCC regulations or use by other wireless devices), the wireless protocol includes multiple timeslots 142A-142E within each frequency channel 140A-140D as seen in FIG. 2. These timeslots 142A-142E occur once within every super frame 144 (i.e. a time period where every timeslot 142A-142E occurs once), providing a predictable time when data can be transmitted by a pair of units 102 and 104. In this respect, the communications protocol can accommodate more data transmissions than would otherwise be possible by only using different frequency channels 140A-140D alone.

Timing Master

Figure 3:
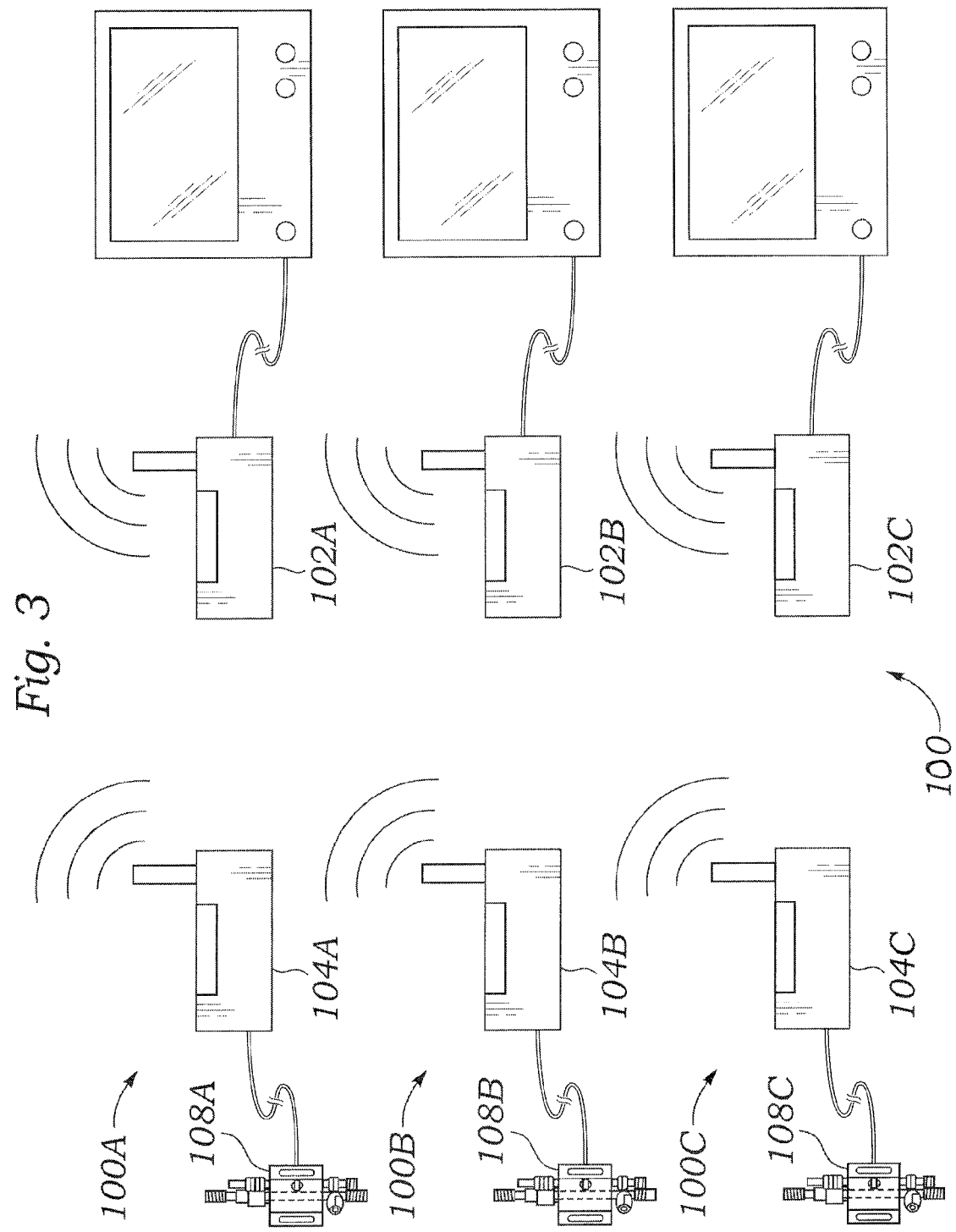
FIG. 3 illustrates a wireless communication system according to a preferred embodiment of the present invention.

The usage of timeslots 142A-142E of each super frame 144 seen in FIG. 2 are controlled by a portable unit 104 that acts as a timing master (i.e. a unit maintaining a master clock by which the time of the timeslots are determined) coordinating the timeslot usage for all communications on a particular frequency channel. In the example of FIG. 1, the portable unit 104 is the timing master, controlling, among other aspects, the timeslot usage on each frequency channel. However, when multiple portable units 104 are present, such as in FIG. 3, one portable unit acts as the timing master for the portable units 104. For example, portable unit 104A controls the timeslot usage for a group of portable units 104B and 104C and thereby controls their transmission times to avoid interference or other communication complications. Generally, the timing master communicates a transmission schedule to other units on the network, informing them of when and how they can communicate on the network (e.g. assigning a timeslot for a particular pair of units).

As a timing master, the portable unit 104A not only transmits sensor data to its associated monitor unit 102A just like all other portable units, but also monitors a control timeslot (i.e. a timeslot reserved for control commands by the timing master), responds to commands and requests by other units 102 and 104 (e.g. a request by a portable unit 104 for a free timeslot), and determines a line of succession among nearby portable units 104 in the event the original timing master no longer qualifies as being the timing master.

The control timeslot is a timeslot, such as any one of timeslots 142A-142E in FIG. 2 that is designated for conveying control data only, allowing and thereby governing the interaction of units 102 and 104 within one system. Preferably, this control timeslot is universally predetermined by the manufacturer for simplicity, such as the first timeslot 142A of every frequency channel. For example, referring to FIG. 3, the portable unit 104C may wish to join a pre-existing frequency channel network controlled by timing master portable unit 104A. To do so, it sends a timeslot request on the control timeslot to the timing master 104A. The timing master then responds on the control timeslot with an appropriate response, such as by indicating an open slot for that frequency or that the frequency channel is full. Since the portable unit 104 is the "master" in the relationship with the monitor units 102, only these portable units 104 will send commands to each other.

Since the control timeslot can be used at any time by any of the portable units 104 to communicate with the timing master, the wireless protocol includes collision detection which prevents multiple control signals sent at the same time from colliding and therefore causing interference on the control timeslot. Generally, the collision detection directs each portable unit 104 to reference its own unique serial number before sending data on the control timeslot, allowing this number to guide its behavior in this regard.

The collision detection protocol is included with all portable units 104 (since all portable units 104 must communicate on the control timeslot to join a frequency channel). The collision detection protocol can generally be described as introducing asymmetrical or irregular transmission behaviors to reduce the likelihood that multiple units 104 will attempt to transmit data at the same time.

This asymmetrical transmission behavior of the collision detection protocol is achieved by irregularly switching the portable unit 104 between two main behaviors: a data transmission mode and a listening mode. In the data transmission mode, the portable unit 104 immediately sends its data message on the control timeslot. In the listening mode, the portable unit 104 listens for communications by other portable units 104 on the control timeslot.

To determine which mode a portable unit 104 irregularly switches into when it has data to transmit, the collision detection protocol looks to the value of the first digit of the unique serial number (i.e. a number unique to each portable unit 104 and generated by the manufacturer). For example, if the serial number consists of only ones and zeros, a one may signal the data transmission mode while a zero may indicate that the portable unit 104 act according to the listening mode. In this respect, the portable unit 104 will either immediately transmit or listen for transmissions on the control slot.

If the portable unit sees a "listening mode digit", it switches to listening mode, ending the mode following a predetermined time after the control slot has been free of any transmissions. At this point, the collision detection protocol again looks to the next digit in the serial number, repeating this cycle until finding a "data transmission mode digit", at which point it transmits its data message. In this respect, irregular intervals of "waiting" can be introduced between portable units 104, reducing the likelihood that units will attempt to transmit at the same time.

After the portable unit 104 first transmits a message containing a desired command, it then waits for a valid response from the timing master. If the response is valid, the portable unit 104 acts accordingly. If the response is not valid, the collision detection protocol will again look to the next digit in its unique serial number and act accordingly, as previously described.

In the event the timing master ceases communications, a line of succession is followed by the units 104 so that another unit 104 takes its place, becoming the new timing master. This line of succession is determined by the current timing master who which creates a ranked list that is frequently updated and distributed to the other units on that frequency channel network. If a portable unit 104 is activated and no timing master is present, that unit will automatically become the timing master for a specific frequency.

This line of succession is achieved, for example, by allowing each unit 102 and 104 of the group to monitor the radio strength signal indicator (RSSI) values, in other words the strength of the radio signal, for all timeslots. These units 102 and 104 transmit the RSSI data to the timing master in the control timeslot. The timing master then uses the RSSI values to calculate and rank each portable unit 104 according to their ability to communicate with all of the units 102 and 104 of the group. Thus, those portable units 104 receiving high RSSI values (i.e. strong radio signals) for other units will be positioned higher on the list. Similarly, other radio signal characteristics can be measured and factored into the preference list, such as the amount of interference in a signal.

Finally, the timing master transmits the succession order back to all of the units 102 and 104. As new pairs of units are added to a frequency channel, the process is repeated or at least repeated for the new pair, allowing the timing master to update the line of succession. Thus, if the current timing master is turned off or otherwise stops transmitting, the next portable unit 104 in the succession line begins to act as a timing master.

Further, the timing master may determine that a portable unit 104 is better positioned than itself to communicate with all of the units of a frequency channel. In this situation, the timing master places that portable unit 104 ahead of itself in the line of succession, causing it to become the new timing master for the frequency channel.

In this respect, a timing master is always present within a single pair of units 102 and 104 or multiple pairs of units 102 and 104, coordinating communications, reducing interference, and promoting efficient data transfer. Additionally, the high RSSI value preference ensures that the next unit to become the timing master is the best unit to receive signals from all units. Further, if a portable unit 104 is the first to start up, it automatically becomes the timing master until additional nearby units are activated and added to the list.

Jumping Frequency Channels

In some situations, the portable unit 104 may decide that it should jump from one frequency channel to another, such as jumping from frequency channel 140A to 140B in the example of FIG. 2. The most common reasons for a frequency channel jump include situations where the portable unit 104 determines there is excessive interference with its transmissions, the portable unit 104 does not reliably receive data from the timing master, the portable unit 104 is directed to jump by the timing master, or the portable unit 104 becomes aware of a nearby unit jumping to a new frequency channel.

To make such a jump, the portable unit 104 transmits a jump message to the timing master on the control timeslot, which then acknowledges the jump message back on the control timeslot. The monitor unit 102 listens for the jump message on both the control timeslot and the allocated sensor data transmission timeslot and jumps with the portable unit 104 to the designated frequency channel. In the event that the monitor unit 102 loses contact with its associated portable unit 104, the monitor unit 102 scans all timeslots of all frequency channels to reestablish a connection.

After the pair jump, the timing master, which maintains a table of RSSI values measured by each unit, determines if there are other pairs of units 102 and 104 in close proximity to the jumping units (i.e. units that have high radio signals above a predetermined threshold as measured by the jumping pair of units 102 and 104). If other pairs are determined to be within a close proximity, the timing master will issue a jump command over the control timeslot, sending them to the same frequency channel as the pair of units 102 and 104 initially jumping. Thus, pairs of units 102 and 104 close to each other will tend to stay on the same frequency channel and therefore within the same group. As previously discussed, maintaining units on the same frequency can prevent bleeding-interference on nearby frequencies.

Frequency Channel Preferences

When a pair of units 102 and 104 activate or decide to jump to a new frequency channel, the portable unit 104 will scan all frequency channels, rank these frequency channels based on various criteria, then attempt to join the most preferred frequency channel. Preferably, the frequency channel preference is primarily determined by the RSSI value (i.e. the strength of the radio signals) of any of the units using a frequency channel.

For example, the portable unit 104 may initially categorize each RSSI value into a predetermined low, medium, or high category. Then, the overall priority for each frequency channel is ranked by giving highest priority to the frequency channels with high RSSI values (i.e. strong radio signals), next those with medium RSSI values or lower, followed by open channels with no radio activity, then those with only low RSSI values (i.e. weak radio signals), followed last by frequency channels with an interfering or jamming frequency. Priority can be further distinguished by increasing the priority of frequency channels with a timing master having a higher RSSI value and by increasing priority for frequency channels including a greater numbers of high and/or medium RSSI values for each timeslot.

When pairs of units are close to each other, their radio transmissions can interfere with or bleed between transmissions between pairs of units on other frequencies. However, when these nearby units are included on the same frequency channel, they are assigned their own timeslot and therefore never transmit at the same time, preventing interference. Thus, grouping nearby pairs of units on the same frequency channel will reduce interference and therefore cause more efficient data transfer and overall network stability.

By following such a frequency channel preference protocol, the portable unit 104 will prefer to join frequency channels in which nearby units 102 and 104 are already communicating on, thus minimizing bleeding of transmissions into adjacent frequencies as previously discussed. Additionally, the portable unit 104 will generally avoid frequency channels with more distant units 102 and 104 or with disrupting interference. Instead, frequency channels with a greater number of strong radio signals are preferred, thus, enhancing the stability of network communications and maximizing signal clarity.

Startup Behavior

Generally, the startup behavior of the wireless communications system 100 includes associating a portable unit 104 and a monitor unit 102 together to facilitate sensor data transfer only between those two units, then locating an acceptable channel for communications.

Figure 4:
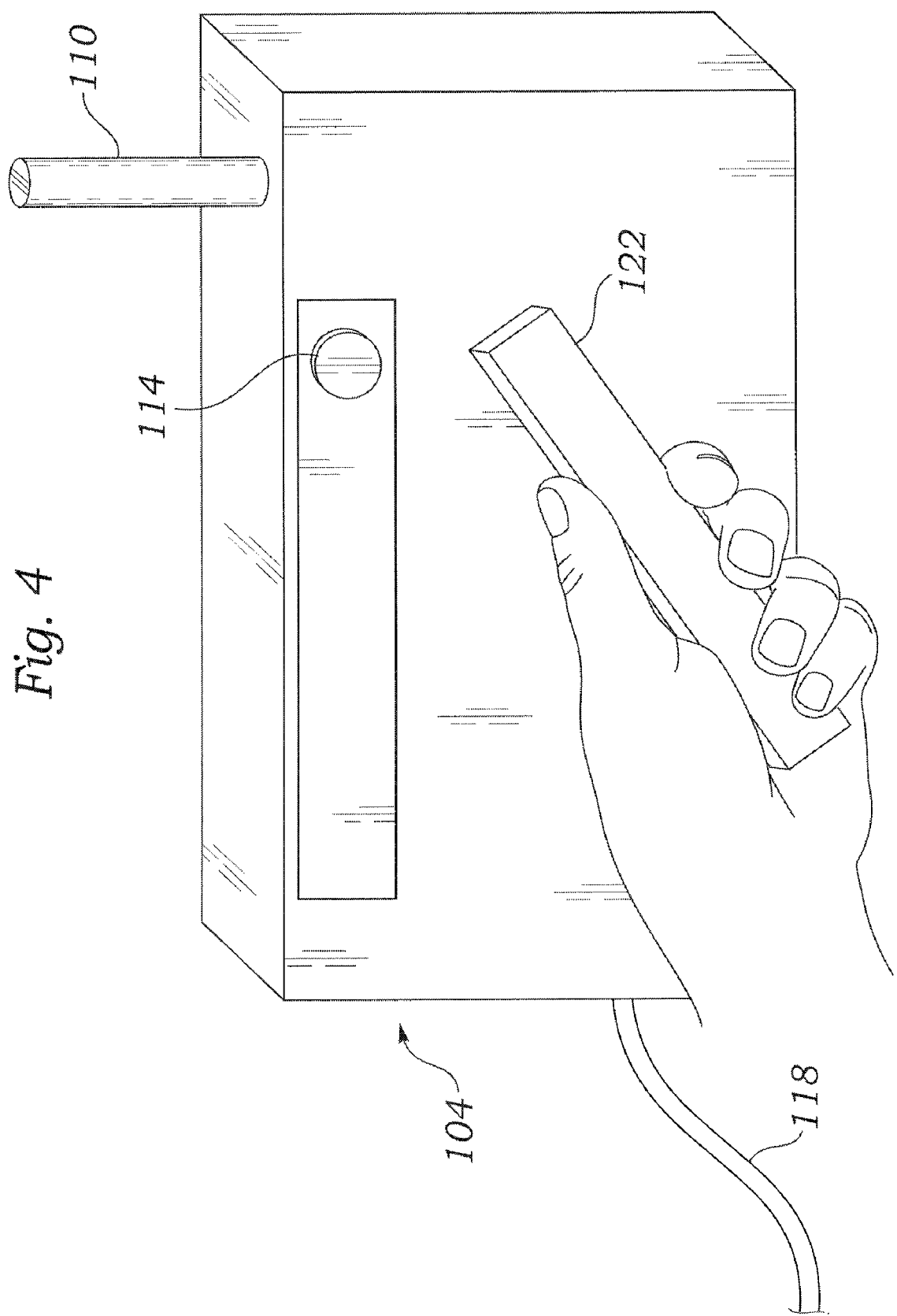
FIG. 4 illustrates an ID tag according to a preferred embodiment of the present invention.

The wireless communications system 100 allows for a portable unit 104 and a monitor unit 102 to be associated or "mated" with each other as a pair to prevent confusion with other pairs operating nearby and to facilitate transmission of sensor data to the desired monitor unit 102. This association is achieved, in a preferred embodiment, by providing an association code to both units 102 and 104 by way of an RFID system, as is known in the art, which allows the units 102 and 104 to initially "find" each other. Each unit 102 and 104 includes a RFID tag reader which can read any one of a series of external RFID tags 122, as seen in FIG. 4. Each RFID tag 122 includes a small radiofrequency transponder which transmits a code when interrogated by the RFID tag readers of the units 102 and 104. In a preferred embodiment, each unit 102 and 104 generally includes two transceivers: a first transceiver for the RFID tag reader which is configured to communicate over a few centimeters and a second transceiver for transmitting sensor data over many meters (e.g. 10 meters). By using two transceivers, the units 102 and 104 communicate different types of information in an efficient manner.

More specifically, the first transceiver (for the RFID tag reader) communicates the RFID data for linking the units 102 and 104 together over a short range with low power frequencies while the second transceiver (for the sensor data) communicates the sensor data over a long range with high power frequencies. This is a more efficient configuration than one where, for example, both the RFID data and the sensor data are transmitted with one long range, high power frequency transceiver. Such a configuration would use more power than otherwise necessary to operate the invention.

Generally, RFID readers are composed of three components: control circuitry, a RFID transceiver 114, 116, and an antenna 110, 112. These three components can operate on a variety of frequencies, such as 125-134 kHz, 13.56 MHz, 902-928 MHz, and 2.4 GHz, depending on the desired characteristics of the system (e.g. transmission range, power consumption, creation of unwanted interference, etc.). With regard to the present invention, there are at least two different ways to configure these components into a suitable RFID reader. However, the main goal is always to maintain relatively low power requirements in order to maximize battery life in the portable unit 104. The first way is a customized approach and the second way is an off-the-shelf approach.

In the customized approach, the control component is provided by the microcontroller that already exists in each of the units 102 and 104. This avoids having two separate control chips in each of the units 102 and 104. An antenna and a transceiver are then selected based on the optimized frequency and power requirements and then mounted on a circuit board internal to the units 102 and 104. The customized approach leads to a RFID reader configuration that is precisely tailored to a desired frequency range and transmitting environment of the units 102 and 104 since both the transceiver and antenna can be individually selected. It also optimizes the power requirements of the units 102 and 104, especially to minimize power consumption of the battery within portable unit 104. The customized approach can also be less expensive than other approaches.

In a preferred embodiment under the customized approach, an acceptable RFID transceiver include the multi-protocol transceiver model S6700 or the TMS3705A, both from Texas Instruments. Additional technical information on these transceiver chips is available from Texas Instruments and is incorporated herein by reference.

As for a suitable antenna in the customized approach, such an antenna will typically vary in size and configuration based on the transmission frequency. For example a 125-134 kHz transmission frequency may operate with a 5 cm diameter air coil of copper wire having about 66 turns or a wire coil wound around a ferrite core, such as the low-Q P-7896 from Dynasys. In another example, higher transmission frequencies can be achieved with an antenna printed directly on the circuit board, such as those described in the technical specifications provided by Texas Instruments literature number 11-08-26-001, the contents of which are hereby incorporated by reference.

In the off-the-shelf approach, each of the RFID reader components (control, antenna, transceiver) are integrated in one reader chip or reader device which can be purchased ready-made or "off-the-shelf" and then added to each of the units 102 or 104. In a preferred embodiment, acceptable reader chips include the SkyeRead M1 from SkyeTek or the Series 2000 Micro Reader from Texas Instruments. Additional technical information on these chips are available through their respective manufacturers and is incorporated herein by reference. Such off-the-shelf reader chips communicate with the host microprocessor of the units 102 or 104 through a standard protocol such as RS-232, TTL, I$^2$C, or SPI, thereby integrating into the circuitry of each unit 102 and 104. While the off-the-shelf approach can lead to an easier integration of an RFID reader into the units 102 and 104 and while they also may provide more consistent performance, such off-the-shelf devices often lead to greater expense than what can be achieved with a customized approach.

Additional information regarding RFID can be found in U.S. Pat. Nos. 6,972,662; 6,956,509; 6,951,596; 6,940,408; 6,903,656; 6,812,841; 6,809,952; and 6,097,622; the contents of each of which are hereby incorporated by reference.

As seen in FIG. 4, the user first moves the RFID tag 122 in close proximity to one of the units 102 and 104, allowing the RFID reader to read the association code transmitted by the RFID tag 122. Next, the same RFID tag 122 is moved in close proximity to the other unit 102 or 104, allowing that unit to also read that code. In this respect, the user causes both units 102 and 104 of the intended pair to receive the same association code unique to that RFID tag 122.

Since electromagnetic interference between closely spaced RFID reader modules of any type (i.e., regardless of whether they are readers based on a customized or an off-the-shelf approach) can cause interference with each other, the present invention preferably controls the RFID transmissions using timeslots. This reduces the possible interference between two RFID reader units. For example, timeslots may be randomly assigned to each unit 102 or 104 prior to use by the consumer, simply reducing the odds that two units will transmit on the same timeslot. Alternatively, a more ordered timeslot system can be used in which each unit 102 and 104 are assigned timeslots, similar to the sensor data timeslot system for transmission of sensor data described below. Other interference reducing techniques can be seen in U.S. Pat. No. 6,566,997, the contents of which are hereby incorporated by reference.

Preferably, the RFID reader is turned off after the two units 102 and 104 have been associated as a pair, and even more preferably immediately after obtaining information from the RFID tag 122. By minimizing the time the RFID reader is transmitting and receiving, power consumption is minimized and thus battery life on the portable unit is maximized. Additionally, any potential interference created by the RFID reader, or other readers of other nearby units 102 and 104, may be minimized since any transmissions on RFID frequencies are minimized.

Alternatively, the RFID tag 122 can be another type of tag or device that can transmit an ID number or code, such as a magnetic code (e.g. a magnetic strip on a credit card) or an optical mechanism (e.g. bar code and reader). Additionally, each RFID tag 122 can be colored or numbered to help distinguish a group of different tags 122.

Once in possession of the association code from the RFID tag 122, the portable unit 104 scans all frequency channels for peak radio signal values, determines a preference for these frequency channels as previously discussed in this application, then attempts to join the most preferred frequency channel. If that frequency channel is completely free (i.e., there are no other units communicating on it), the portable unit 104 becomes the timing master and begins transmitting as such on that frequency channel. If the preferred frequency channel already includes a timing master, the portable unit 104 negotiates an open timeslot from the timing master, if available.

Once a timeslot has been determined, the portable unit 104 transmits a command to create a new partnership, which includes the association code from the RFID tag 122. The monitor unit 102 also scans all frequency channels for a command to create a new partnership. If that new partnership command includes the same association code obtained by the monitor unit 102 from the RFID tag 122, the monitor unit 102 responds back to that portable unit 104 with the monitor unit's unique identification serial number. Once received by the portable unit 104, it reciprocates by sending the monitor unit 102 its unique identification serial number.

As previously described, the unique identification serial number is a permanent identification number designated during the manufacturing process that is unique to all units and is included in any communications from that unit. After exchanging unique identification serial numbers, both units 102 and 104 can recognize signals sent from each other, since all data messages include this identification serial number. When the pairing is complete and the monitor unit 102 has jumped to the same frequency channel as the paired portable unit 104, the portable unit 102 begins transmitting sensor data.

Once units 102 and 104 are paired and communicating, they retain this partnership until one unit is powered down or not responding to communications for a predetermined time. After such a termination of this partnership, the partnering can be reestablished as previously described.

Since the ID number of the RFID tag 122 is only used temporary, i.e. only for a short duration while the unique serial numbers of each unit 102 and 104 are exchanged, an RFID tag 122 can be reused to associate other units 102 and 104 as pairs. Thus, while RFID tags 122 using different ID's can be used to associate different units 102 and 104 (e.g. tag A can be used for pair 1 and tag B can be used for pair 2), a single RFID tag 122 can also be used to associate each pair as they are activated (e.g. tag A can be used for pair 1 and tag A can be used for pair 2 once pair 1 has finished pairing).

The RFID tag 122 can also include additional information used by each unit 102 and 104. For example, an RFID tag 122 may specify a specific frequency channel that both units may initially search on to locate each other during the previously described startup behavior. This may reduce the time needed for each unit to "find" each other, since only one frequency is searched, leading to quicker and more reliable startup behavior. Alternately, each RFID tag 122 may specify other relevant transmission control data, such as which frequency channels, timeslots, or RFID timeslots the units 102 and 104 can communicate on. In this respect, different units 102 and 104 can be restricted by the user to different frequency channels. Such frequency restrictions may be desired to reduce interference between the units 102 and 104 and other unrelated hospital equipment.

Power Down

To turn off the units 102 and 104, the user can press a power down button on either unit 102 and 104 causing that unit to send a message to the other unit indicating that it will power down. Once the receiving unit responds to the original unit, both units power down. In this respect, turning off one unit will also cause the other unit to turn off, saving battery power and reducing radio interference for other nearby pairs.

For example, a user presses a power down button on a portable unit 104, causing the portable unit 104 to send a power down message to its paired monitor unit 102. Once the monitor unit 102 receives this power down message, it sends a reply power down message back to the portable unit 104.

Message Definition

In a preferred embodiment, the transmitters within each portable unit 104 and monitor unit 102 can transmit at 153 kbps (6.5 μs/bit) which allows about 8919 bits per superframe of 58.3 ms (7 samples at a sample rate of 120 samples/sec). This allows 26 slots and a single control slot per frequency. With a 500 kHz channel bandwidth, there could be up to 15 frequency channels which could allow 390 possible transmission positions. With an estimated maximum realistic loading of 33%, approximately 130 pairs of units could be reasonable in a typical ICU area.

More reliable performance could be achieved with transmission of redundant data. At the same latency, the transmission of redundant data would reduce the number of slots.

An increase in latency to 100 ms (15300 bits) would mean 12 samples per superframe. The message size of the portable unit 104 would increase by 40 bits for data and 1 bit for larger slot numbers, and the number of slots would increase to 41 slots and 1 control slot.

FIGS. 5-8 represent example message structures for some of the communications used by the wireless communication system 100. For example, FIG. 15 illustrates the message structure of the portable unit, FIG. 6 illustrates the message structure of the stationary unit, FIG. 7 illustrates the control message structure of the portable unit, and FIG. 8 illustrates the control message structure of the stationary unit.

Example Startup Operation

To better illustrate the present invention, the startup behavior of the previously described preferred embodiment will be further discussed below.

In operation, the portable unit 104 is activated by the user, activating the RFID reader within the portable unit 104. The user then selects an RFID tag 122 and moves it within proximity of the RFID reader, transmitting the association code contained within the RFID tag 122.

The portable unit 104 begins a scan of all frequency channels, measuring the peak RSSI value for each channel generally and for the timing master on each channel (if present). Also during this scan, the portable unit 104 stores the specific timeslot of each frequency channel.

If the portable unit 104 detects a frequency channel with a high RSSI value (i.e. a signal strength indicating another portable unit 104 is nearby) the portable unit 104 will listen for a predetermined amount of time to the timeslot of the unit 104 creating that signal in an attempt to "follow" that signal. By staying on the same frequency, frequency "bleeding" will be reduced since each nearby unit will be transmitting at different times.

For example, if the portable unit 104 hears that the nearby unit recently jumped to this frequency channel, the portable unit 104 will wait for sensor data to be transmitted before proceeding. If the nearby unit 104 initiates a jump command, the portable unit 104 begins to scan the frequency channels again.

Once the scan has been completed, the portable unit 104 follows predetermined frequency channel selection rules. Table 1 below provides some example rules that portable unit 104 may follow, in order of decreasing preference.

TABLE 1

| Frequency Channel Measurement | Rule |
| --- | --- |
| A frequency channel includes a high signal strength on at least one timeslot. | Portable unit must join on an open timeslot. If no open timeslots, another frequency channel is chosen. |
| A frequency channel includes an intermediate signal strength on at least one timeslot. | Portable unit will join the frequency channel if it has the timing master with the strongest signal. |
| A frequency channel does not include transmissions on any slots. | Portable unit will select the frequency channel and become the timing master for that channel. |
| A frequency channel includes only weak signal strengths. | Portable unit will avoid joining this frequency channel. |
| A frequency channel includes jamming or interfering signals. | Portable unit will avoid joining this frequency channel. |

If the frequency channel is empty, the portable unit establishes that it is the timing master and begins transmitting a "new link" message containing the association code of the RFID tag 122. If the frequency channel is not empty, the portable unit 104 transmits a timeslot request message on the control timeslot of that frequency channel. When the timing master responds with an allowable timeslot number, the portable unit 104 begins transmitting a "new link" message containing the association code of the RFID tag 122. If the monitor unit 102 does not respond within a predetermined period of time, the portable unit 104 will jump to the "next best" frequency channel.

The monitor unit 102 is preferably activated by the user shortly after the portable unit 104. The same RFID tag 122 is moved within proximity of the RFID reader within the monitor unit 102, transferring the association code within the RFID tag 122 to the memory of the monitor unit 102.

Next, the monitor unit 102 scans all of the frequency channels measuring peak RSSI values and RSSI values of the timing master of each channel. If one channel includes portable units with high signal strengths, the monitor unit 102 will listen on this frequency channel for the new link signal from the portable unit 104. If the portable unit 104 is not heard on this frequency channel, the monitor unit 104 will rotate through the remaining frequency channels, listening for the portable unit 104.

When the monitor unit 102 finds the new link message transmitted by the portable unit 104, each unit 102 and 104 respond with their unique serial numbers. These unique serial numbers allow each unit 102 and 104 to know which unit it is paired to, and therefore which unit to transmit to.

Once the portable unit 104 and the monitor unit 104 have connected to each other and exchanged unique serial numbers, the portable unit 104 can either jump to a more desirable frequency or begin transmitting sensor data to the monitor unit 102.

Alternative ID Linking Embodiments

In addition to the encoded RFID tag 122, other preferred devices and methods are possible for "linking" or "mating" a portable unit 104 with a monitor unit 102.

In one preferred embodiment, each unit 102 and 104 can be activated and directed to send linking radiofrequency signals. Each unlinked unit can display the units available for linking, by either presenting this data on an LCD screen, displaying a light that blinks in the same pattern as the newly activated unit, or by presenting a series of sounds (e.g. beeps) that sound in the same pattern as the newly activated unit. In this respect, the unlinked units 102 and 104 can communicate, either visually or aurally, a linking or mating ID, allowing the user to determine if a specific link is appropriate.

In another preferred embodiment, each unit 102 and 104 may allow a user to "make up" and type in a linking ID into two units 102 and 104 that are desired to be linked. The units 102 and 104 may allow multiple digits to be entered, a combination of colors linking to numbers, letters, or similar input methods.

In another preferred embodiment, the units 102 and 104 may include the ability to directly transmit a linking or mating ID code to each other when in close proximity. For example, each unit 102 and 104 can include a RFID tag within its structure, as well as an RFID reader. Thus, a portable unit 104 and a monitor unit 102 can simply be set to a "linking" mode and moved within close proximity of each other. In another example, such a direct communication of a linking ID may be achieved by providing infrared transmitters and receivers or a direct electrical connection (e.g. data cable).

In another preferred embodiment, the units 102 and 104 may transfer a linking ID by way of IC chips or "smart cards" (i.e. cards with memory chips or magnetic storage media) that plug into reader slots on each of the units 102 and 104. In this manner, a linking ID can either be preprogrammed on the smart card, or one unit 102 or 104 can initially write a linking ID onto a card, then that newly written linking ID can be read by another unit 102 or 104, causing them to link.

In yet another preferred embodiment, a patient unit can be included near the patient, such as on an IV pole or bed, which provides a common "platform" that supplies mounting positions, power connections, and communication connections for each portable unit 104 that is connected to a patient.

In another preferred embodiment, the previously described linking ID communications methods can also include a visual or auditory confirmation method. Since the units 102 and 104 may often be used in an area with many other pairs of units 102 and 104, a user may wish to confirm that the linking ID procedure created an appropriate link between the desired units 102 and 104. Additionally, a new user, such as a nurse who recently began their shift, may wish to examine or confirm pre-existing links. For example, the user may press a confirm button on one unit 102 and 104 which causes both of the linked units in the pair to flash a matching but randomly generated sequence of flashing lights or sounds. In this way, the user can easily determine if two units are linked.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of organizing wireless communications comprising:
    providing a portable unit connected to a medical sensor;
    providing a monitor unit connected to a monitor;
    transmitting a first wireless signal from said portable unit to said monitor unit; and
    controlling a second wireless signal transmitted from said monitor unit using said first wireless signal;
wherein said controlling a second wireless signal includes causing said second wireless signal to be transmitted according to a predetermined schedule.

2. The method of claim 1, wherein said causing said second wireless signal to be transmitted according to a predetermined schedule includes determining said predetermined schedule during operation of said portable unit and said monitor unit.

3. The method of claim 1, further comprising updating said predetermined schedule during operation of said portable unit and said monitor unit.

4. The method of claim 1, wherein said controlling a second wireless signal further includes causing said second wireless signal to be transmitted on a pre-selected communication timeslot.

5. A method of organizing wireless communications comprising:
provinding a portable unit connected to a medical sensor;
providing a monitor unit connected to a monitor;
transmitting a first wireless signal from said portable unit to said monitor unit; and
controlling a second wireless signal transmitted from said monitor unit using said first wireless signal;
wherein said controlling a second wireless signal includes causing said second wireless signal to be transmitted on a predetermined communication frequency and a predetermined timeslot within said communication frequency.

6. A method of organizing wireless communications comprising:
providing a portable unit connected to a medical sensor;
providing a monitor unit connected to a monitor;
transmitting a first wireless signal from said portable unit to said monitor unit; and
controlling a second wireless signal transmitted from said monitor unit using said first wireless signal;
further comprising coordinating wireless transmissions from a plurality of other portable units with said portable unit.

7. A wireless sensor system comprising:
a first slave unit connectable to a monitor for relating sensor data to said monitor, said first slave unit including a first wireless transceiver; and
a timing master unit connectable to a medical sensor, said timing master unit including a second wireless transceiver for controlling transmissions of at least said first slave unit;
wherein controlling transmission of at least said first slave unit includes communicating a transmission schedule to said first slave unit.

8. A wireless sensor system comprising:
a first slave unit connectable to a monitor for relating sensor data to said monitor, said first slave unit including a first wireless transceiver; and
a timing master unit connectable to a medical sensor, said timing master unit including a second wireless transceiver for controlling transmissions of at least said first slave unit;
further comprising a plurality of portable units each connectable to a medical sensor and a plurality of slave units each connectable to a vital signs monitor; the transmissions of said plurality of portable units and said plurality of slave units controlled by said first timing master unit.

9. The wireless sensor system of claim 8, wherein any one of said plurality of portable units can become said timing master unit.

10. A wireless communication system comprising:
a monitor unit including a first wireless transceiver, said monitor unit connected to a vital monitor; and
a portable unit connected to a sensor;
said portable unit including a processor for identifying a wireless transmission schedule and a second wireless transceiver for communicating said wireless transmission schedule to said monitor unit.

11. The wireless communication system of claim 10, wherein said processor in said portable unit includes a protocol to communicate said wireless transmission schedule to a plurality of portable units and a plurality of monitor units.

12. The wireless communication system of claim 10, wherein said transmission schedule includes a transmission frequency and a timeslot on which said monitor unit is to communicate.

13. The wireless communications system of claim 10, wherein said transmission schedule is transmitted on a predetermined timeslot.

14. The wireless communications system of claim 10, wherein said processor determines said transmission schedule when said portable unit is designated as a timing master.

15. The wireless communications system of claim 14, wherein designating of said portable unit as said timing master is based on a detection by said processor of at least one radio signal strength measurement.

16. A method of organizing wireless communications comprising:
providing a first portable unit connected to a medical sensor;
providing a first monitor unit connected to a monitor;
searching for a second portable unit controlling at least part of a wireless communications protocol; and
controlling at least part of said wireless communications protocol with said first portable unit if said searching for said second portable unit is unsuccessful.

17. The method of claim 16, further comprising:
providing additional portable units; and
identifying which of said portable units to assume control of at least part of said wireless communications protocol in the event such assumption of control becomes necessary.

18. The method of claim 17, wherein identifying which of said portable units to assume control includes ranking said portable units based on a wireless signal strength.

19. The method of claim 16, wherein controlling at least part of said wireless communications protocol with said first portable unit if said searching for said second portable unit is unsuccessful includes designating a transmission schedule for at least said first portable unit.

20. The method of claim 19, wherein said controlling at least part of said wireless communication protocol includes designating a transmission schedule for a plurality of portable units.

21. The method of claim 16, wherein said searching for said second portable unit is unsuccessful when a wireless signal strength of said second portable unit is below a threshold value.

22. A method of organizing wireless communications comprising:
providing a first portable unit connectable to a medical sensor;
providing a first monitor unit connectable to a monitor;
activating said first portable unit and said first monitor unit;
scanning a plurality of frequencies with said first portable unit;
evaluating said plurality of frequencies based on a plurality of predetermined preferences;
selecting a transmission frequency based on said evaluating said plurality of frequencies;
communicating said transmission frequency to said first monitor unit; and
causing transmission of information on said transmission frequency between said first portable unit and said first monitor unit.

23. The method of claim 22, wherein said evaluating of said plurality of frequencies based on a plurality of predetermined preferences includes evaluating a plurality of signal strengths on said frequencies.

24. The method of claim 23, wherein said evaluating of a plurality of signal strengths on said frequencies includes categorizing a plurality of wireless signals based on radio signal strength and ranking said plurality of frequencies.

25. The method of claim 22, wherein said evaluating of said plurality of frequencies based on a plurality of predetermined preferences includes increasing preference for a frequency of said plurality of frequencies based on radio signal strength.

26. The method of claim 22, wherein said evaluating said plurality of frequencies based on a plurality of predetermined preferences includes increasing preference for a frequency of said plurality of frequencies based on a number of portable units within a close proximity to said first portable unit.

27. A method of organizing wireless communications comprising:
- providing a plurality of portable units, each portable unit being connectable to a medical sensor and including a wireless transceiver;
- providing a plurality of monitor units being connectable to a monitor and including a wireless transceiver;
- creating a line of succession based on characteristics of a wireless signal of each of said plurality of portable units; and
- selecting a first portable unit from said plurality of portable units as a timing master based on said line of succession.

28. The method of claim 27, wherein said creating of a line of succession includes measuring a radio signal strength of said plurality of portable units on a frequency channel.

29. The method of claim 28, further comprising:
- causing said first portable unit to become unavailable; and
- selecting a second portable unit from said plurality of portable units based on said line of succession.

30. The method of claim 27, wherein said creating a line of succession based on characteristics of a wireless signal of each of said plurality of portable units includes storing said line of succession in a current timing master.

31. The method of claim 27, further comprising transmitting said line of succession to said plurality of portable units.

32. A method of organizing wireless communications comprising:
- providing a first portable unit connectable to a medical sensor and having a first wireless ID tag reader;
- providing a first monitor unit connectable to a monitor and having a second wireless ID tag reader;
- moving a first ID tag near either one of said first portable unit and said first monitor unit to transmit an association code contained within said ID tag;
- moving said first ID tag near the other of said first portable unit and said first monitor unit to transmit said association code contained within said ID tag;
- transmitting a wireless signal including said association code with a first wireless transceiver contained within said first portable unit;
- receiving said wireless signal including said association code with a second wireless transceiver contained within said first monitor unit; and
- creating a partnership between said first portable unit and said first monitor unit based on said second wireless transceiver sensing said association code.

33. The method of claim 32, wherein said creating a partnership between said first portable unit and said first monitor unit further comprises:
- transmitting a first portable unit serial number to said first monitor unit and storing said portable unit serial number in a first monitor unit memory;
- transmitting a first monitor unit serial number to said first portable unit and storing said monitor unit serial number in a first portable unit memory.

34. The method of claim 33, further comprising transmitting a sensor data packet including said first portable unit serial number from said first portable unit to said first monitor unit.

35. The method of claim 32, wherein said moving a first ID tag near one of said first portable unit and said first monitor unit to transmit an association code contained within said ID tag includes transmitting said association code by radio frequency communication.

36. A wireless sensor system comprising:
- a first unit connectable to a monitor for relating sensor data to said monitor, said first unit including a first wireless transceiver and a first wireless RFID transceiver; and
- a second unit connectable to a medical sensor, said second unit including a second wireless transceiver for transmitting a first data signal to said first unit and including a second RFID transceiver.

37. The wireless sensor system of claim 36, wherein said second wireless transceiver controls transmissions of at least said first unit.

38. The wireless sensor system of claim 36, further comprising an RFID tag readable by said first RFID transceiver and said second RFID transceiver.

39. The wireless sensor system of claim 36, wherein said first RFID transceiver and said second RFID transceiver transmit on a frequency selected from 125-134 kHz, 13.56 MHz, 902-928 MHz, and 2.4 GHz.

* * * * *

UNITED STATES PATENT AND TRADEMARK OFFICE
CERTIFICATE OF CORRECTION

| | | |
|---|---|---|
| PATENT NO. | : 7,595,723 B2 | |
| APPLICATION NO. | : 11/449511 | |
| DATED | : September 29, 2009 | |
| INVENTOR(S) | : Heitzmann et al. | |

It is certified that error appears in the above-identified patent and that said Letters Patent is hereby corrected as shown below:

Col. 15 lines 44-56

Claim 8 should read:

A wireless sensor system comprising:

a first slave unit connectable to a monitor for relating sensor data to said monitor, said first slave unit including a first wireless transceiver; and a timing master unit connectable to a medical sensor, said timing master unit including a second wireless transceiver for controlling transmissions of at least said first slave unit;

further comprising a plurality of portable units each connectable to a medical sensor and a plurality of slave units each connectable to a ~~vital signs~~ monitor; the transmissions of said plurality of portable units and said plurality of slave units controlled by said first timing master unit.

Col. 15 lines 60-67

Claim 10 should read:

A wireless communication system comprising:

a monitoring unit including a first wireless transceiver, said monitor unit connected to a ~~vital signs~~ monitor; ~~and~~ a portable unit connected to a sensor; <u>and</u>

Signed and Sealed this

Second Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,595,723 B2  Page 1 of 1
APPLICATION NO. : 11/449511
DATED : September 29, 2009
INVENTOR(S) : Heitzmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 475 days.

Signed and Sealed this

Twenty-eighth Day of September, 2010

David J. Kappos
*Director of the United States Patent and Trademark Office*